United States Patent
Schmidt (10) Patent No.: US 10,820,832 B2
(45) Date of Patent: Nov. 3, 2020

(54) COUGH DETECTION, ANALYSIS, AND COMMUNICATION PLATFORM

(71) Applicant: Quvium UK Ltd, Finchley, London (GB)

(72) Inventor: Steven P. Schmidt, Salem, NH (US)

(73) Assignee: Quvium UK Ltd, London (GB)

( * ) Notice: Subject to any disclaimer, the term of this patent is extended or adjusted under 35 U.S.C. 154(b) by 0 days.

(21) Appl. No.: 14/336,180

(22) Filed: Jul. 21, 2014

(65) Prior Publication Data

US 2015/0025417 A1    Jan. 22, 2015

Related U.S. Application Data (60) Provisional application No. 61/856,803, filed on Jul. 22, 2013.

(51) Int. Cl.
*A61B 5/08* (2006.01)
*A61B 5/00* (2006.01)
(Continued)

(52) U.S. Cl.
CPC .......... *A61B 5/0823* (2013.01); *A61B 5/0022* (2013.01); *A61B 5/6822* (2013.01);
(Continued)

(58) Field of Classification Search
CPC .............. A61B 7/003; A61B 7/04; A61B 7/00
(Continued)

(56) References Cited

U.S. PATENT DOCUMENTS

| | | |
|---|---|---|
| 2005/0090725 A1 | 4/2005 | Page et al. |
| 2006/0277037 A1 | 12/2006 | Woodcock et al. |

(Continued)

FOREIGN PATENT DOCUMENTS

| | | |
|---|---|---|
| AU | 2014293401 B2 | 2/2016 |
| CN | 102043893 A | 5/2011 |

(Continued)

OTHER PUBLICATIONS

Australian Examination Report No. 1 dated Apr. 27, 2018 cited in Application No. 2014293401, 5 pgs.
(Continued)

*Primary Examiner* — Daniel L Cerioni
(74) *Attorney, Agent, or Firm* — Bekiares Eliezer LLP (57) ABSTRACT

A cough detection, analysis, and communication platform may be provided. The platform may comprise methods, systems, and a devices for detecting, analyzing, and communicating cough detection data. A cough detection device may comprise at least one microphone and analytic firmware used to employ methods of detecting, analyzing, and communicating the cough detection data. The analytic software may be updated to use the appropriate algorithms for an individual or corresponding demographic based on, for example, age and disease, with abnormal cough frequency components, abnormal cough frequency profiles, and alert thresholds. The cough detection device may be configured to communicate cough detection data to a server. The server, in turn, may be operative to process and communicate the data to a third party, such as, for example, a physician. Systems may further be operative to provide a user interface (e.g., mobile or web applications) for interfacing with the platform.

8 Claims, 10 Drawing Sheets

(51) Int. Cl.
*G06F 19/00* (2018.01)
*A61B 7/00* (2006.01)
*G16H 15/00* (2018.01)

(52) U.S. Cl.
CPC .......... *G06F 19/3418* (2013.01); *A61B 7/003* (2013.01); *A61B 2560/0209* (2013.01); *G16H 15/00* (2018.01)

(58) Field of Classification Search
USPC ........................................................ 600/586
See application file for complete search history.

(56) References Cited

U.S. PATENT DOCUMENTS

| | | | |
|---|---|---|---|
| 2008/0114220 | A1 | 5/2008 | Banet et al. |
| 2009/0043580 | A1 | 2/2009 | Mozer et al. |
| 2009/0216127 | A1 | 8/2009 | Gavriely |
| 2011/0015702 | A1 | 1/2011 | Ternes et al. |
| 2011/0112442 | A1 | 5/2011 | Meger et al. |
| 2011/0125044 | A1 | 5/2011 | Rhee et al. |
| 2011/0184250 | A1 | 7/2011 | Schmidt et al. |
| 2011/0245688 | A1 | 10/2011 | Arora et al. |
| 2011/0257935 | A1 | 10/2011 | De Graaf et al. |
| 2012/0265024 | A1 | 10/2012 | Shrivastav et al. |
| 2012/0265272 | A1 | 10/2012 | Judkins |
| 2012/0302898 | A1 | 11/2012 | Zhang et al. |
| 2013/0060100 | A1 | 3/2013 | Wurm et al. |
| 2014/0128767 | A1 | 5/2014 | Hoest et al. |
| 2014/0249378 | A1* | 9/2014 | Chan .................. A61B 5/0823 600/301 |
| 2015/0245788 | A1 | 9/2015 | Schmidt |

FOREIGN PATENT DOCUMENTS

| | | |
|---|---|---|
| CN | 202235373 U | 5/2012 |
| CN | 105517493 A | 4/2016 |
| EP | 0956823 A1 | 11/1999 |
| GB | 253406 A | 6/1926 |
| GB | 2516768 A | 2/2015 |
| GB | 2536699 A | 9/2016 |
| JP | H0998964 A | 4/1997 |
| JP | 2002500078 A | 1/2002 |
| JP | 2009233103 A | 10/2009 |
| WO | 9934864 A1 | 7/1997 |
| WO | WO2006/129098 | 12/2006 |
| WO | WO 2006/129098 A2 | 12/2006 |
| WO | WO2007/001431 | 1/2007 |
| WO | WO 2007/001431 A2 | 1/2007 |
| WO | 2007108322 A1 | 9/2007 |
| WO | WO 2008/152433 | 12/2008 |
| WO | 2009080040 A1 | 7/2009 |
| WO | 2012092562 A1 | 7/2012 |
| WO | WO2012/117393 | 9/2012 |
| WO | 2013040485 A1 | 3/2013 |
| WO | 2014141277 A1 | 9/2014 |
| WO | 2015013183 A3 | 1/2015 |
| WO | 2015020886 A1 | 2/2015 |
| WO | 2016014135 A1 | 1/2016 |

OTHER PUBLICATIONS

European Search Report dated Feb. 17, 2017 cited in Application No. 14829899.5, 10 pgs.
International Search Report dated Apr. 8, 2015 cited in Application No. PCT/US15/28128, 2 pgs.
International Search Report dated Jan. 13, 2015 cited in Application No. PCT/US14/47405, 4 pgs.
United Kingdom Examination Report dated Nov. 26, 2014 cited in Application No. 1412909.2, 1 pg.
United Kingdom Examination Report dated Aug. 12, 2015 cited in Application No. 1412909.2, 1 pg.
Chinese First Office Action dated Feb. 2, 2018 cited in Application No. 201480047192.X, 5 pgs.
Japanese Notice of Reasons for Refusal dated May 8, 2018 cited in Application No. 2016-529810, 12 pgs.
Chinese Second Office Action dated Dec. 12, 2018 cited in Application No. 201480047192.X, 6 pgs.
Japanese Notification of Reasons for Refusal dated Apr. 9, 2019 cited in Application No. 2016-529810, 8 pgs.
Chinese Third Office Action dated Jul. 17, 2019 cited in Application No. 201480047192.X, 9 pgs.
Chinese Fourth Office Action dated Jan. 15, 2020 cited in Application No. 201480047192.X, 12 pgs.
Japanese Final Notice of Reasons for Refusal dated Mar. 3, 2020 cited in Application No. 2016-529810, 6 pgs.
European Second Examination Report dated Apr. 1, 2020 cited in Application No. 14 829 899.5, 6 pgs.

* cited by examiner

COUGH DETECTION, ANALYSIS, AND COMMUNICATION PLATFORM

PRIORITY CLAIM

The present application claims the benefit of U.S. Provisional Patent Application No. 61/856,803, entitled "Cough Detection," invented by Steven P. Schmidt, and filed to the United States Patent and Trademark Office on Jul. 22, 2013. The disclosure of the provisional application is incorporated herein by reference.

RELATED APPLICATION

Related U.S. patent application Ser. No. 13/011,394, filed by the same inventor and entitled "Early Warning Method and System for Chronic Disease Management," is incorporated herein by reference.

TECHNICAL FIELD

The technical field of the present disclosure generally relates to medical devices and remote health-care services.

BACKGROUND

Patients who have chronic lung disease may experience regular coughing. Sudden increases in their regular coughing frequencies may be an early indicator of respiratory compromise (infection) or impending exacerbation event such as, for example, an asthma attack for people with asthma. In various cases (e.g., Cystic Fibrosis, Asthma, COPD, Pulmonary Fibrosis, Bronchitis, Respiratory infection, Lung Cancer, GERD, and other diseases affecting normal lung operation), a strong indicator of respiratory compromise is an increase in cough frequency which may be due to pathophysiology in the lungs from increasing cough sensitivity and a response to cell influx into lungs. For example, in an impending asthma attack coughing may be an increase in a patients coughing rate from a regular rate of, for example, approximately one cough per two hours to a much higher rate. This increased cough frequency may begin to occur approximately three hours before an exacerbation event ("the attack") in normal case or, for hypersensitive individuals, as late as half an hour before the attack.

Doctor supplied treatment plans have an intervention strategy to prevent a full blown attack at the sign of worsening symptoms (e.g. the increased cough rate). However, these treatment plans may only work if the doctor or patient are aware of the worsening symptoms and act upon this in a timely manner timely act upon this.

An early warning may encourage the patient to seek early treatment. Early treatment, in turn, with rescue medication (e.g., an inhaler) or removal of the exacerbation trigger (e.g., emotional stress such as crying, air pollution, etc.) may impede the full impact of the exacerbation event. Impeding the full impact of the exacerbation event may decrease the likelihood of emergency room visits and hospitalizations for the patient.

Unfortunately some patients, such as children and the elderly, often ignore their early symptoms until early treatment measures are no longer effective, making conventional intervention strategies more likely to fail. Consequently, there is a need for effective and efficient early symptom detection devices that operate passively with minimal patient intervention or noticeability.

BRIEF SUMMARY

This brief summary is provided to introduce a selection of concepts in a simplified form that are further described below in the Detailed Description. This brief summary is not intended to identify key features or essential features of the claimed subject matter. Nor is this brief overview intended to be used to limit the claimed subject matter's scope.

A cough detection, analysis, and communication platform may be provided. The platform may include methods, systems, and a devices for detecting, analyzing, and communicating cough detection data. A cough detection device of the platform may comprise at least one microphone and an analytic software used to employ methods of detecting, analyzing, and communicating the cough detection data.

Consistent with embodiments of the present disclosure, data collected by the cough detection device (e.g., cough frequency) may then be communicated to at least one server. The server may, in turn, be operative to process and communicate the received data to an interested party, such as, but not limited to, a physician. Having the user's cough-frequency date, the physician may then act on the received information in order to, for example, assess the user symptoms and take appropriate action.

The platform may further include a user interface (e.g., mobile or web applications) for enabling users, physicians, and other entities to interface with the platform. For example, a user may access the user interface to configure the parameters and settings of the detection device, including, but not limited to, for example, alert settings. Similarly, a physician may access the user interface in order to, for example, view the processed cough detection data and recommend, through the interface, a treatment for the user. In turn, the user may access the interface to view the physician's recommendations.

Both the foregoing brief summary and the following detailed description provide examples and are explanatory only. Accordingly, the foregoing brief summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicant. In addition, the drawings may contain other marks owned by third parties and are being used for illustrative purposes only. All rights to various trademarks and copyrights represented herein, except those belonging to their respective owners, are vested in and the property of the Applicant. The Applicant retains and reserves all rights in their trademarks and copyrights included herein, and grants permission to reproduce the material only in connection with reproduction of the granted patent and for no other purpose.

In the drawings.

DETAILED DESCRIPTION

The following detailed description refers to the accompanying drawings. Wherever possible, the same reference numbers are used in the drawings and the following description to refer to the same or similar elements. While embodiments of the invention may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the invention. Instead, the proper scope of the invention is defined by the appended claims. The present disclosure contains headers. It should be understood that these headers are used as references and are not to be construed as limiting upon the subjected matter disclosed under the header.

I. Detection Device Design

Embodiments of the present disclosure may provide a cough frequency detection device operative to detect, analyze, and communicate a user's coughing frequency. The detection device may be further operative to provide an indication upon a detection of an increased coughing rate. The indication may serve as an early warning of a physiological cascade of lung problems leading to an exacerbation event. The exacerbation event may be, for example, but not be limited to, an asthma attack.

The detection device may be integrated with, by way of non-limiting example, a pendant, watch, pocket FOB, and a zipper attached FOB. The form of the detection device may vary with considerations of a user's demographics, such as age and gender. The detection device may be small, portable, and have a substantially long battery life. In some embodiments, the detection device may be rechargeable, while in other embodiments the detection device may be disposable.

Figure 1:
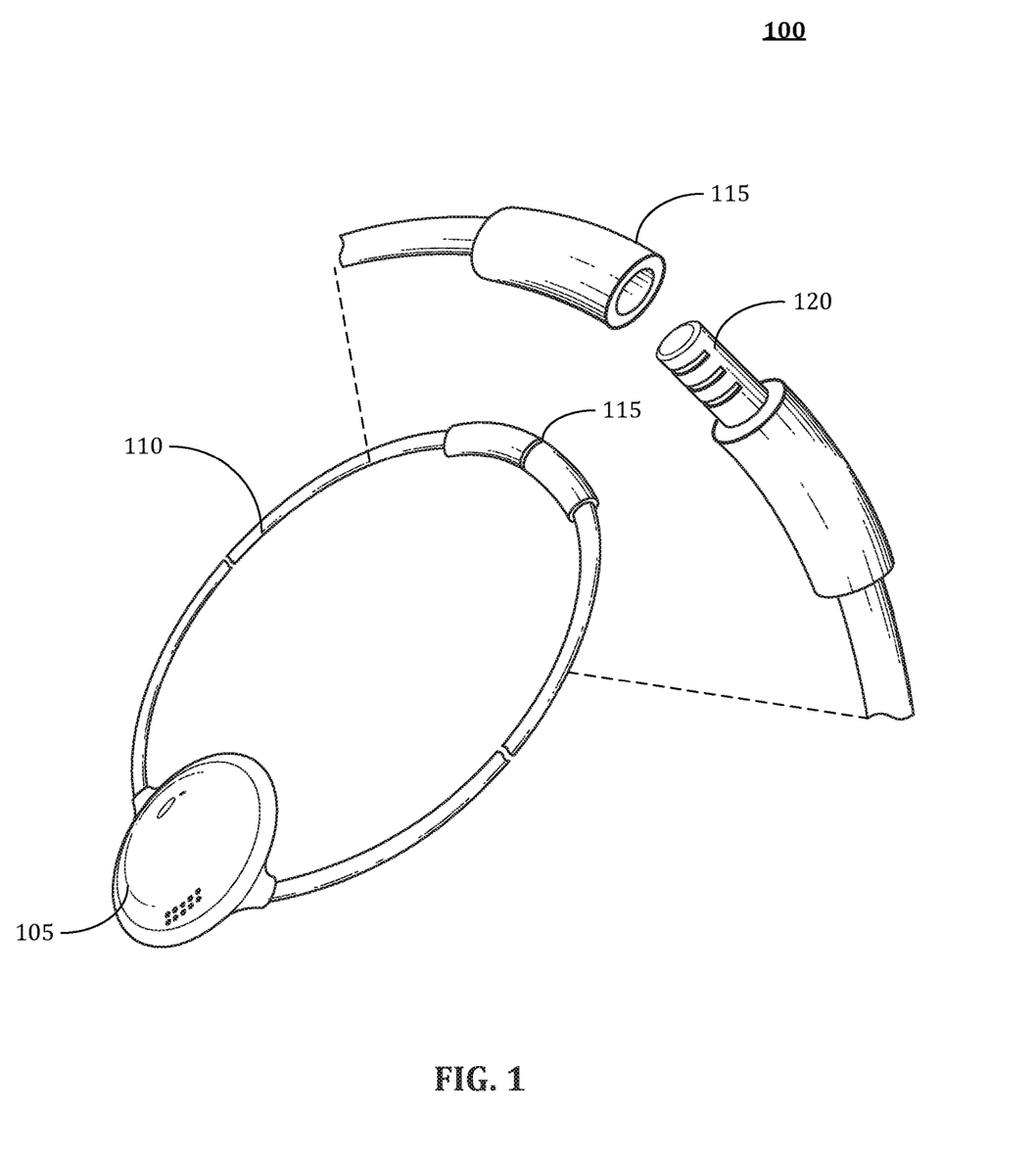
FIG. 1 illustrates a first embodiment of a cough detection device.
Figure 2:
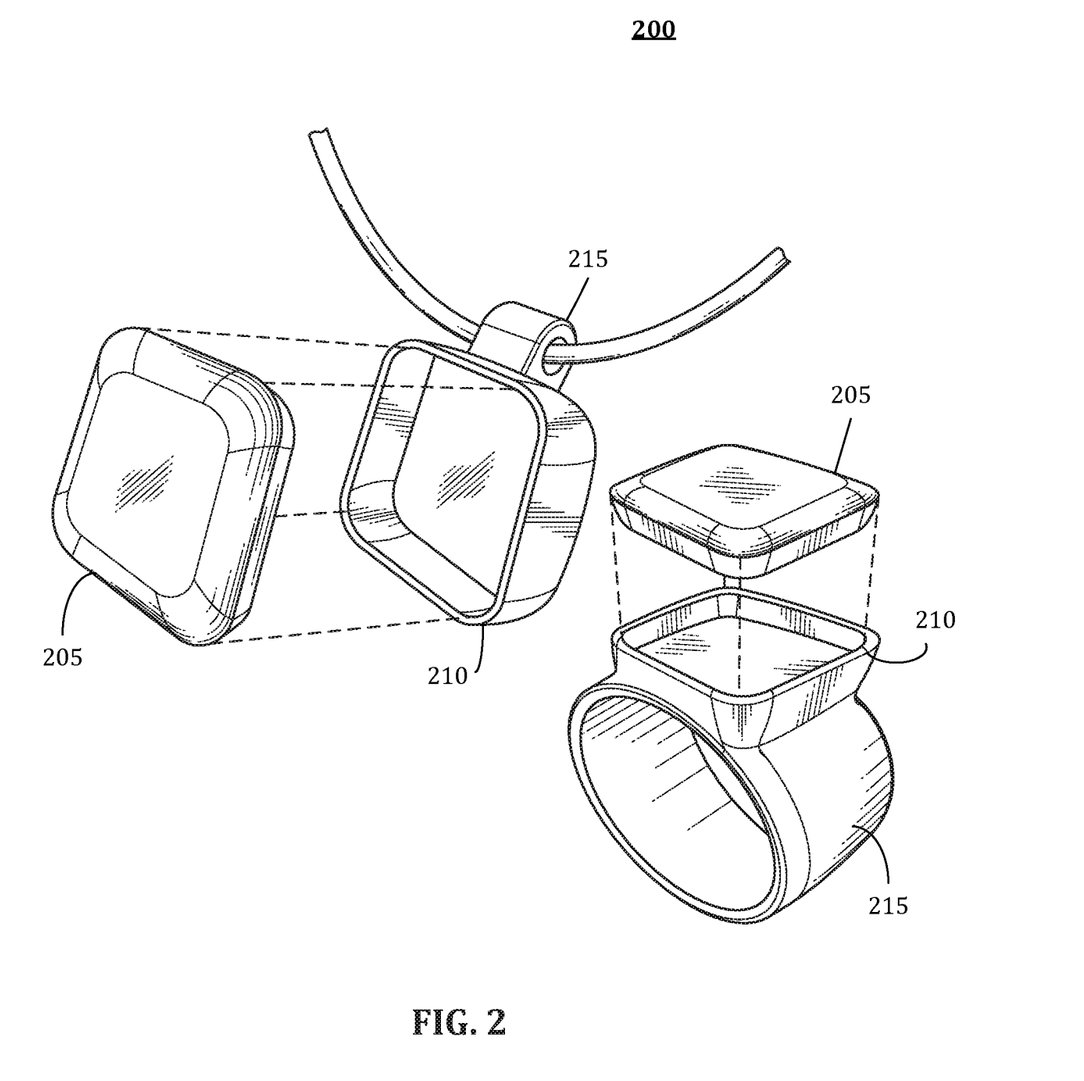
FIG. 2 illustrate a second embodiment of a cough detection device.
Figure 3A:
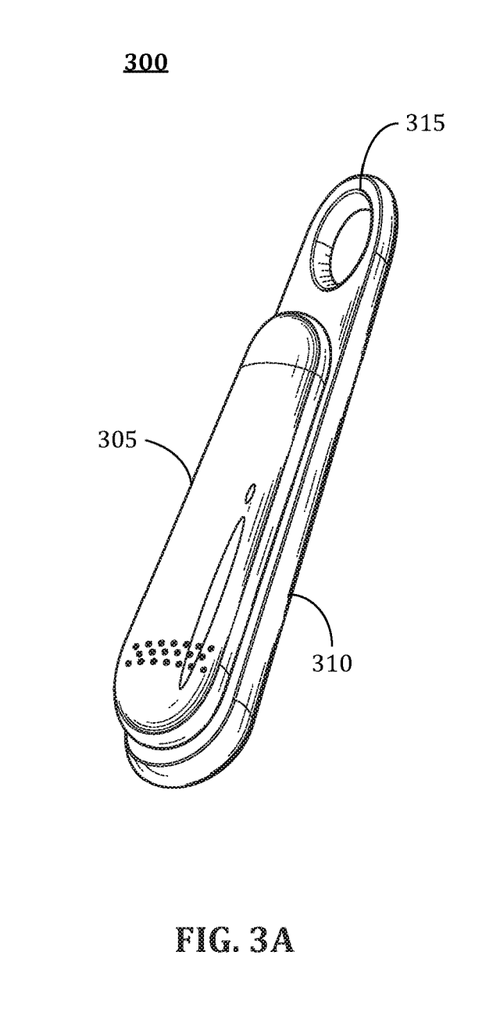
FIG. 3A-3C illustrates a third embodiment of a cough detection device.
Figure 3B:
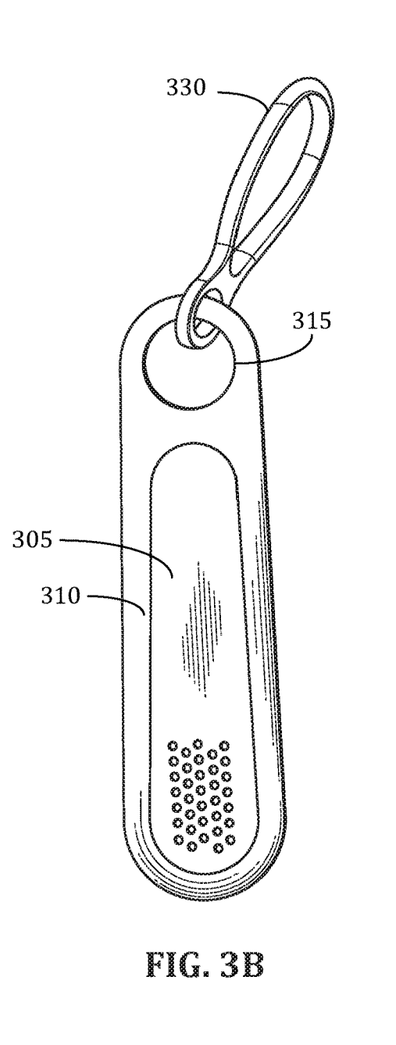
Figure 3C:
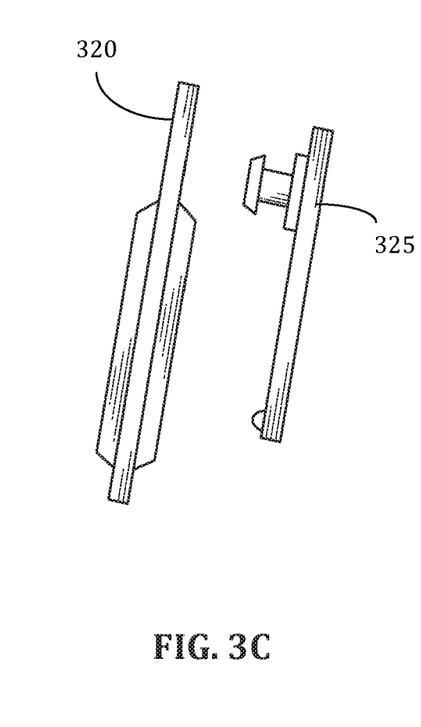

FIGS. 1-3 illustrates various embodiments of the cough detection device. As shown in FIG. 1, detection device 100 may be worn by a user around a user's neck. Detection device 100 may be integrated into various accessories that may be configured to be worn by a user.

For example, in some embodiments, the device 100 may be integrated with a housing 105, a bracing means 110 and a clasp 115. Housing 100 may be comprised of, but not limited to, for example, a rubber and/or plastic material designed to a house the device components for providing and interfacing with the methods and systems of the present disclosure. The bracing means 105 may provide a mechanism to secure device 100 to the user. The mechanism may comprise, for example, a necklace, a bracelet, a ring, or any other suitable article that may be worn by the user. The mechanism may further serve to provide an electronic interface (e.g., wiring and circuitry) from the housing 105 to the clasp 115.

In addition to securely fastening the device to the user, clasp 115 may be configured to serve as, for example, a port 120. Port 120, in turn, may be configured to serve as a charging device or, in some embodiments a communications port (e.g., a universal serial bus (USB) port or similar computing interface). The port may provide energy to the device and/or exchange information between device 100 and an external system as will be detailed below, at least in reference to FIG. 4.

Still consistent with embodiments of the present disclosure, the detection device may be designed for insertion into different user accessories. For example, as shown in FIG. 2, a detection device 200 may comprise a detachable module 205. Detachable module 205 may comprise a housing for the detection device components. The housing may be insertable into a socket 210. Socket 210 may be configured to attach to a bracing means 215. Bracing means 215 may be designed as, or an attachable portion of, for example, but not limited to, a necklace, a ring, or a bracelet.

FIG. 3 illustrates yet another embodiment of a detection device 300. Detection device 300 may be comprised of a detection module 305 having a housing for the detection device components. The housing may be configured to be inserted into a socket 310 comprised of, for example, a mounting ring 310. Mounting ring 315 may be configured to attach to, for example, a user accessory 330. In some embodiments, mounting ring 315 may comprise a port 320. Port 320 may serve as an attachment means to detection device 300. In some embodiments, the port 320 may be configured to couple detection module 300 into an electronic interface such as, for example, but not limited to a snap-in power receptacle or communications interface (e.g., electronics module 325).

In various other embodiments, the detection device of the present disclosure may be associated with a software. The software be embodied in, for example, a mobile application, a web application, a server application, and/or a desktop application. Through communication means detailed at least with reference to FIG. 4 below, the software may be configured to provide and display a plurality reports associated with the data received from the detection device. The reports may include, for example, a combination for graphical and textual elements representing data gathered from the detection device and other processed metrics. Additionally, the reports may be integrated with information from other measuring/monitoring devices to help clarify underlying causes (e.g., a Fitbit® report identifying exercise level).

The software may be further configured to send alerts (e.g., telecommunications including, but not limited to, for example, email, SMS, telephonic alerts) to selected parties. The selected parties may comprise, but not be limited to, friends and relatives, emergency contacts, or the user's physicians who have interest in the user's health condition. Through the software, a user may define a plurality of third parties that are to be contacted in the event an increased cough rate has been detected by the device. Furthermore, the user may configure a message to be communicated to those third parties along with the data.

As will be further detailed below, the software may enable a user to adjust various settings associated with the device, including, but not limited to, for example, a base-line waveform, threshold detection levels, communication rules, alert settings, permitted parties, and the like. In some embodiments, the software may be installed onto a mobile computing device (e.g., a smartphone) in operative communication with the device. The software may be operative with various elements of the mobile computing device, such as, but not limited to, microphones, global positioning elements, cell tower communication, accelerometers, internet connectivity and audio, visual, and tactile feedback mechanisms.

Still consistent with embodiments of the present disclosure, the location of the detection device may be tracked using, for example, global positioning elements of the mobile computing device in communication with the detection device. In turn, the cough detection information received with the detection device may be associated with the user's location as derived from the mobile computing device. Having the user's location, a third party who may receive an alert issued by the detection device may be better enabled to provide emergency on-site assistance to the user. Similarly, in some embodiments, a microphone of the mobile computing device may be used in conjunction with a microphone of the detection device. Employing both microphones as a source of input may lead to better cough detections.

In various embodiments, the software may further comprise an individual's personalized treatment plan, for example, a person's asthma action plan. The asthma action plan may provide helpful guidance to the user to properly interpret and act upon symptoms. Moreover, the software may be configured to display predictive analytics associated with the cough detection information. These analytics may be provided by a third-party physician, for example, or computationally derived by the external device.

Consistent with embodiments of the present disclosure, the user's physician may access the software (via, for example, the web application) to review the information received and derived from the user's detection device. In turn, the physician may diagnose and prescribe a treatment for the user. The prescribed treatment may serve as an input to the software, which, in turn, may be communicated to the user by means of, for example, the user's mobile application.

II. Operating Environment

Figure 4:
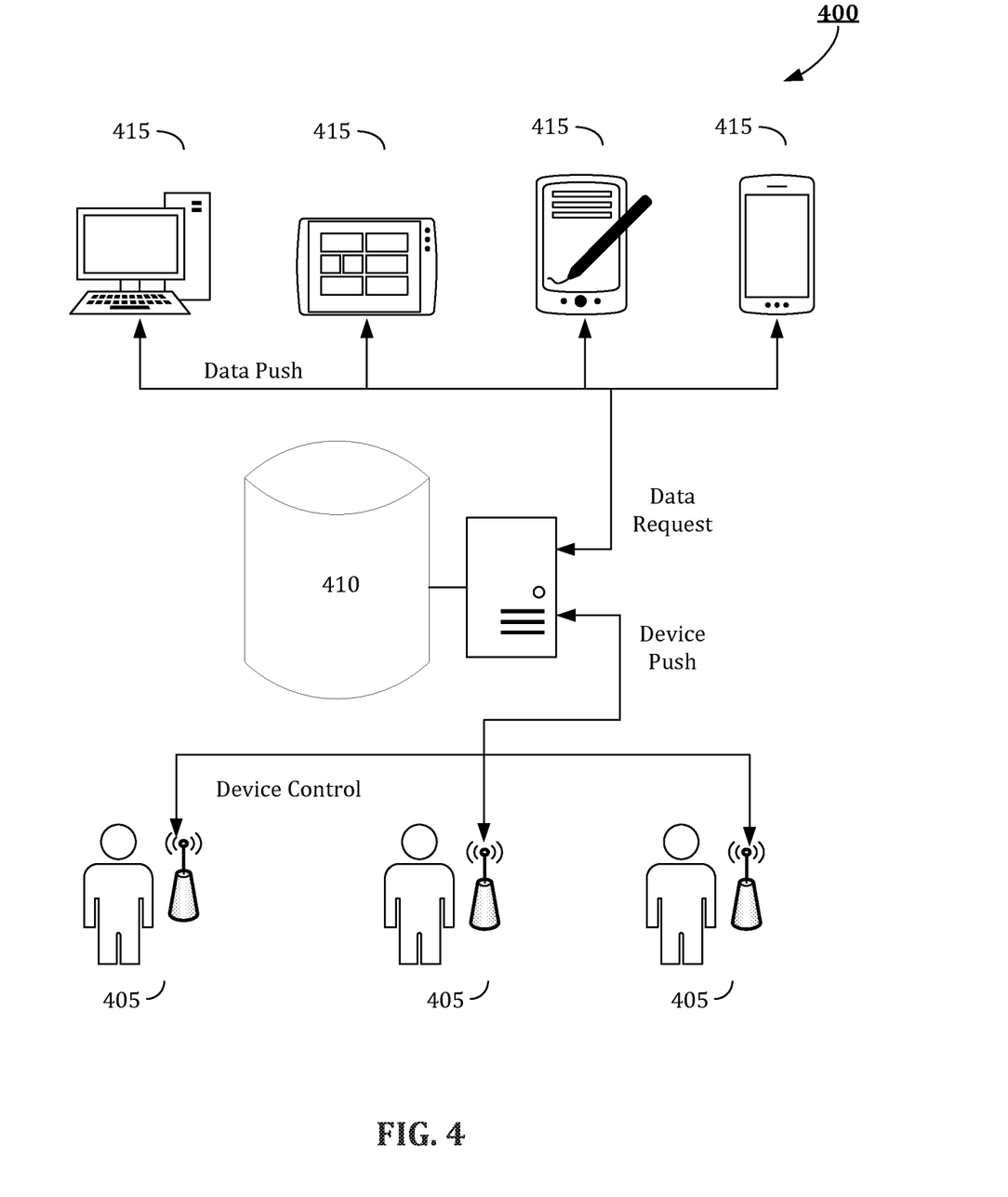
FIG. 4 illustrates an operating environment for a platform consistent with embodiments of the present disclosure.

FIG. 4 illustrates an embodiment of an operating environment 400 for the cough detection, analysis, and communications platform of the present disclosure. The platform may comprise detection devices 405. Detection devices 405 may be, for example, the cough detection devices described with reference FIG. 1-3.

Detection devices 405 may comprise a communications module operative to communicate cough detection data to a centralized server 410. The communications module may be enabled to communicate using Wi-Fi, Bluetooth, cell-tower, broadband, and other telecommunications circuitry to provide communication with centralized server 410. Centralized server 410 may be in operative communication with detection devices 405 via, for example, a telecommunications channel such as, but not limited to, for example, local area network, a wide area network, an internet connection, an/or a cloud computing environment.

Not shown in FIG. 4, detection devices 405 may be further configured to employ an intermediary channel in order to connect to server 410. For example, the communications module of detection devices 405 may only be configured for interaction in a Bluetooth or Wi-Fi communications protocol, yet, in some embodiments, centralized server 410 may not accessible through these protocols. Accordingly, detection devices 405 may employ a Wi-Fi and/or Bluetooth enabled communications module to communicate data to a mobile computing device (e.g., the user's smartphone). The mobile computing device may have mobile application of the platform the installed thereon. In turn, the mobile computing device may be configured communicate the data received from the detection device to centralized server 410, receive data from centralized server 410, and provide data back to the detection device 405.

Server 410 may be operative to process the data received from the detection device 405 (either directly or indirectly through the mobile computing device) and communicate the processed data in accordance to the various embodiments of the present disclosure. The processed data may be received at a user-interface (UI) 415 consistent with embodiments of the present disclosure. As mentioned above, UI 415 accessible by the user of the device or a third party, such as, for example, a physician, administrator, relative, or the detection device user via, for example, a web application or a mobile application consistent with embodiments of the present disclosure.

III. Platform Operation

Figure 5:
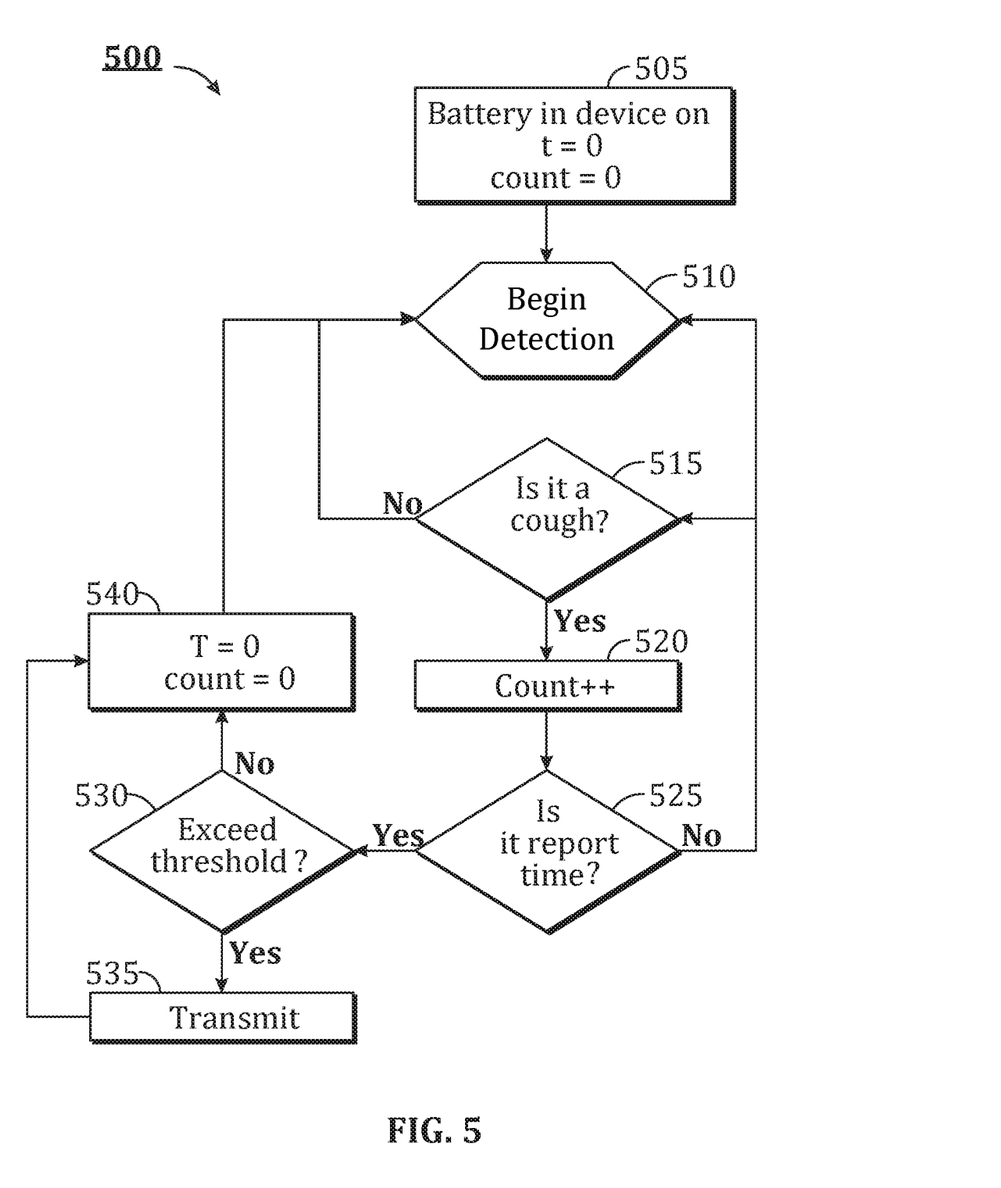
FIG. 5 illustrates a flow chart of a method for providing the platform consistent with embodiments of the present disclosure.
Figure 9A:
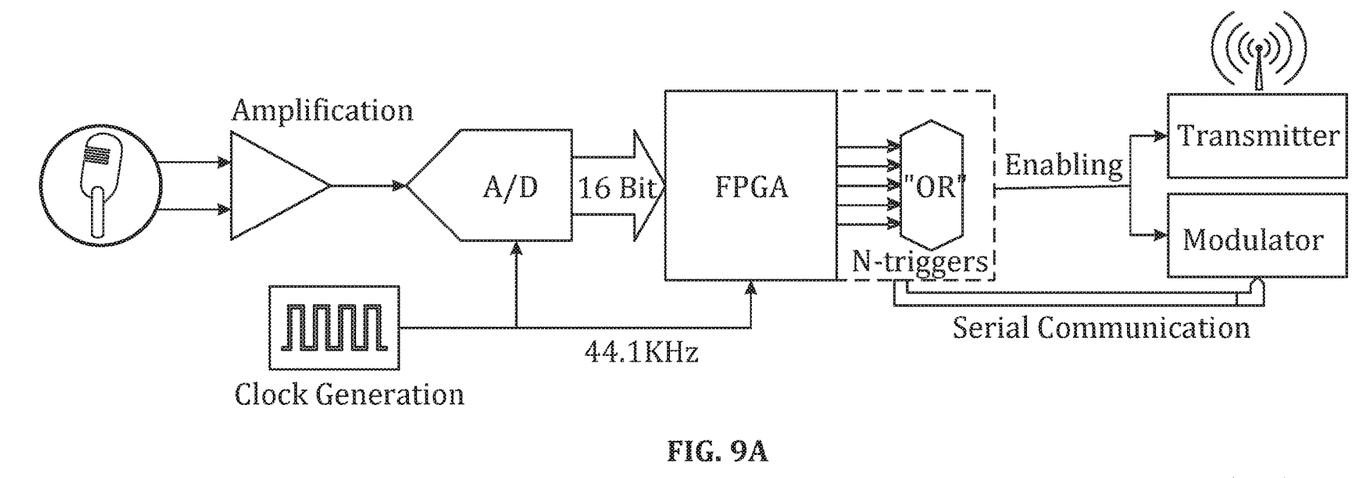
FIGS. 9A-9B illustrates architectures of a detection device consistent with embodiments of the present disclosure.
Figure 9B:
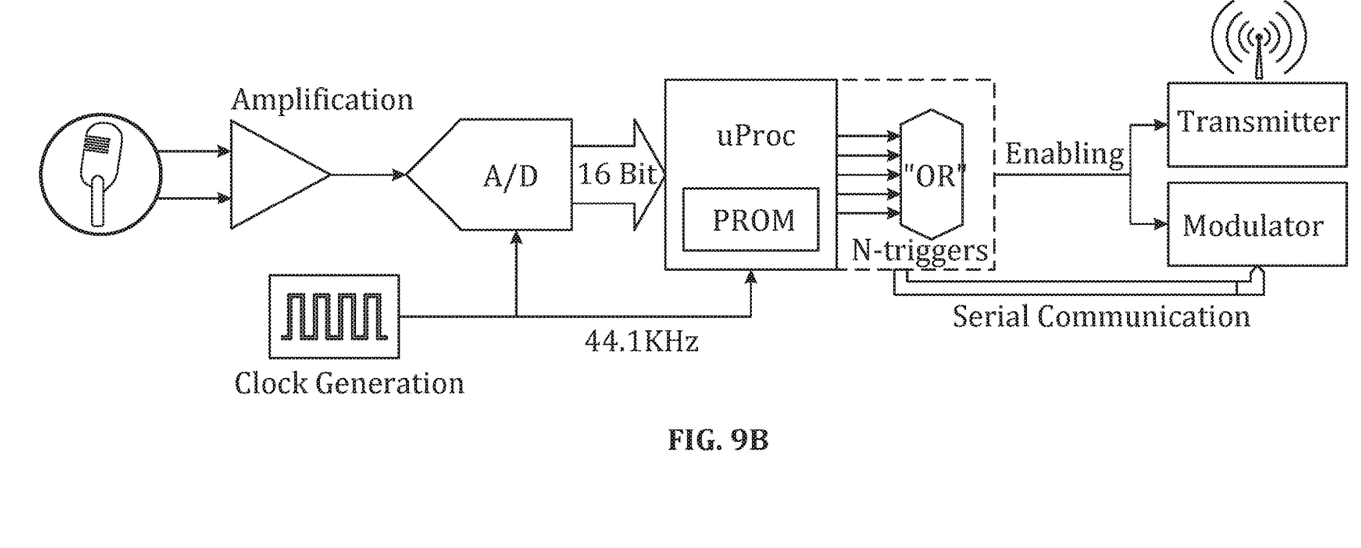

FIG. 5 is a flow chart setting forth the general stages involved in a method 500 consistent with embodiments of the disclosure for providing the cough detection, analysis, and communications platform of the present disclosure. Still consistent with embodiments of the present disclosure, method 500 may be implemented by a combination of hardware elements (e.g., counters, timers, FPGA chips, etc.) and/or software elements (e.g., smartphone application, firmware, etc.) as shown in FIGS. 9A-9B.

Figure 10:
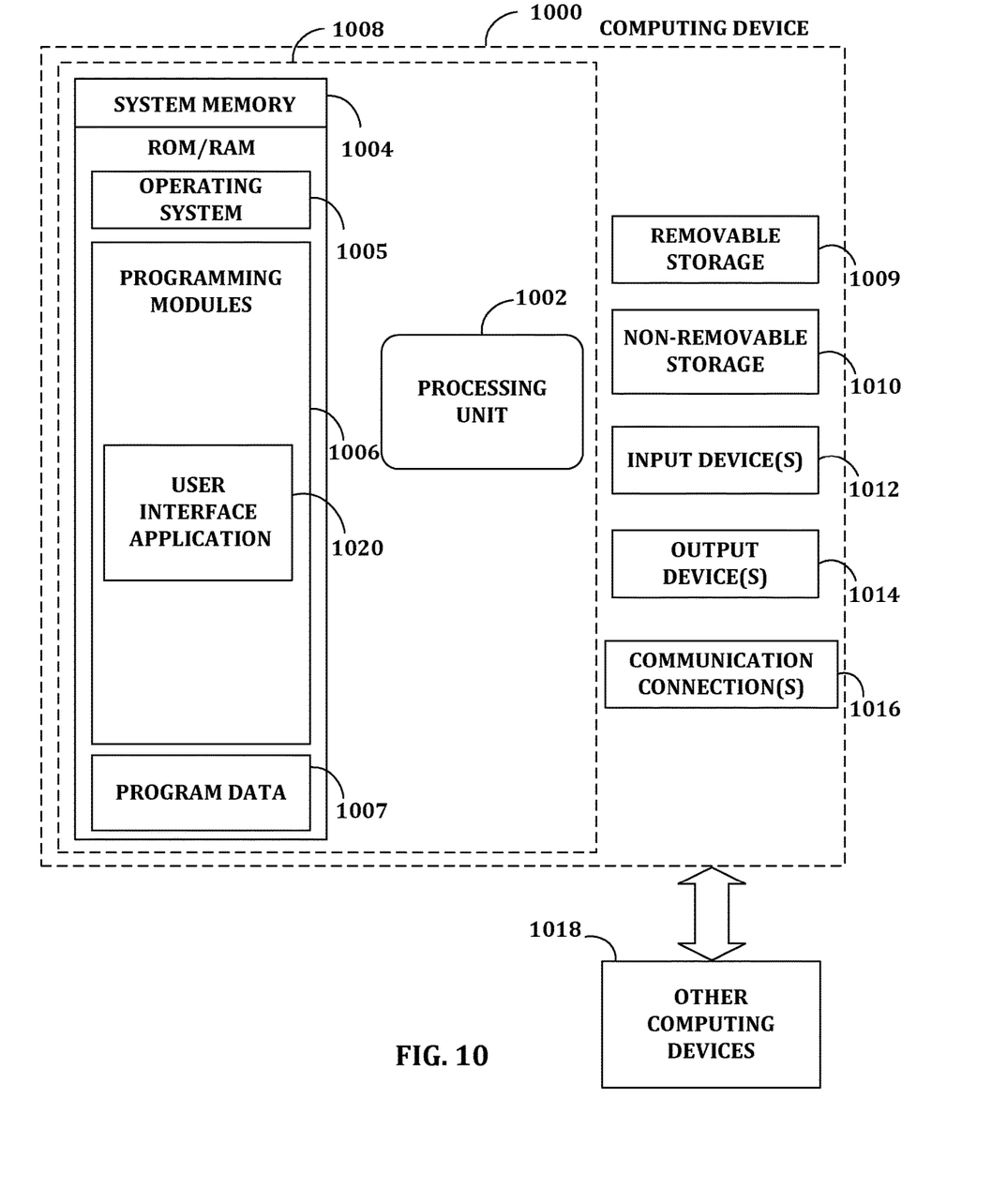
FIG. 10 illustrates a computing device consistent with embodiments of the present disclosure.

Moreover, in some embodiments, method 500 may be performed by computing deice 1000 illustrated in FIG. 10. In these embodiments, detection device 405 may serve as remote microphone that transmits a signal to the computing device 1000 (e.g., a mobile computing device/users smartphone via a Bluetooth connection) which may then, in turn, perform the processing and communications of method 500. In other embodiments, a first portion of the processing disclosed in method 500 may be performed by the detection device 406, while a second portion of the processing may be performed by the mobile computing device.

Though the stages illustrated by the flow charts are disclosed in a particular order, it should be understood that the order is disclosed for illustrative purposes only. Stages may be combined, separated, reordered, and various intermediary stages may exist. Accordingly, it should be understood that the various stages illustrated within the flow chart may be, in various embodiments, performed in arrangements that differ from the ones illustrated. Moreover, various stages may be added or removed from the flow charts without altering or deterring from the fundamental scope of the depicted methods and systems disclosed herein. Ways to implement the stages of method 500 will be described in greater detail below.

The method may begin at stage 505 where detection device 405 may be turned on. Device 405 may be turned on by activation of an on-off switch or activating a battery contact. In embodiments where the device 405 is configured to be in communication with a proximately located mobile computing device (e.g., a user's smartphone), device 405 may be registered with the mobile computing device once turned on. In certain embodiments of the present disclosure, device 405 may always be on, but running in a passive detection state.

Upon detecting a trigger in the passive detection state, device 405 may enter an active detection state. The trigger may comprise, but not be limited to, for example, a microphone pick-up of a sound exceeding a predetermined threshold. The sound may be an indication of a disease exacerbation trigger. Once triggered, device 405 may be configured to operate at the active detection state for a preset period of time.

In the active detection state, a counter and a timer may be set to a value of 0, and cough detection may begin at stage 510. A microphone input of device 405 may be used to detect sounds. As will be described with greater detail below with reference to FIGS. 6-8, a software or firmware running on the device may employ various cough detection algorithms to distinguish coughs from other detected sounds.

Once a sound exceeding the threshold is detected, device 405 may proceed to stage 515 where it may employ the cough detection algorithms to determine whether the detected sound comprises a cough. The cough detection algorithms may be further configured to ascertain whether the detected sound is likely to be a cough. Although an exact detection may not always be made, an approximation or estimate may be still be useful in some applications of the present disclosure (e.g., where the coughing rate is so high that misrecognition may be a non-issue).

If it is determined that the detected sound is not a cough, device 405 may return to detection stage 510. If it is determined that the detected sound is a cough, device 405 may proceed to stage 120 where it may register the cough by incrementing a counter.

From stage 520 where the counter is incremented, device 405 may advance to stage 525 where it checks the timer to determine if the predetermined period of time has expired. If detection time has not expired, the device returns to detection stage 510, and the timer continues to run while the counter continues to be incremented for each detected cough. If detection time has expired, device 405 may proceed to stage 530 where it determines whether the cough counter has exceeded a preset threshold. If the cough counter has exceeded the threshold, device 405 may proceed to stage 535 where it transmits the cough count to server 410.

Consistent with various embodiments, device 405 may be configured to transmit other data in addition to the cough count, such as, but not limited to, historical count information, time information, and location information. As will be detailed below, the transmitted data may comprise a waveform of the detected sounds or an interpretation of the waveform. Moreover, in embodiments where device 405 is configured with other health monitoring utilities, such as heart rate, blood pressure, and blood sugar levels, the device may be operative to transmit corresponding readings with those utilities as well.

As mentioned above, device 405 may communicate with server 410 via an intermediary channel provided by a mobile computing device in communication with device 405. For example, device 405 may provide data to the mobile computing device, which may then, in turn, relay the data to a cloud-based server or third parties defined by the user. In various other embodiments, device 405 may be operative to transmit data directly to server 410.

Once the information is transmitted, device 405 may advance to stage 540 where it may reset the timer and cough counter, and proceed to stage 510 where it may continue in the active detection state for another cycle. In some embodiments, the cough counter may not be reset, and the threshold in stage 530 may be compared to a second threshold corresponding to a two period cycle of detection.

Consistent with embodiments of the present disclosure, different cough count and time combinations may correspond to different signals being transmitted by device 405. For example, if a first quantity of coughs were detected in a first cycle (e.g., six coughs were detected in the first fifteen minute cycle) and another quantity of coughs were detected in the second cycle (e.g., six coughs were detected in a second fifteen minute cycle), a first signal may be transmitted. Similarly, if, for example, ten coughs were detected in the first fifteen minute cycle and another fifteen coughs were detected in the second fifteen minute cycle, a second signal may be transmitted.

In this way, different cough rates may be configured to cause a transmission of different signals. The signals may be preset signals which may, in turn, each trigger different actions at by server 410 or a mobile computing device in operative communication with device 405. Moreover, because signal transmission may substantially impact battery drainage, a power management configuration may cause the transmission circuitry of the detection device to turn on in periodic short bursts as needed.

If in stage 530 it is determined that cough counter has not exceeded the threshold, then detection device may proceed to stage 540, reset the timer and cough counter, and enter into the passive detection state. When the device enters back into the passive state, an "all clear" signal may be transmitted. Additional information, such as a low batter warning, may be transmitted when necessary.

IV. Signal Processing

Figure 6A:
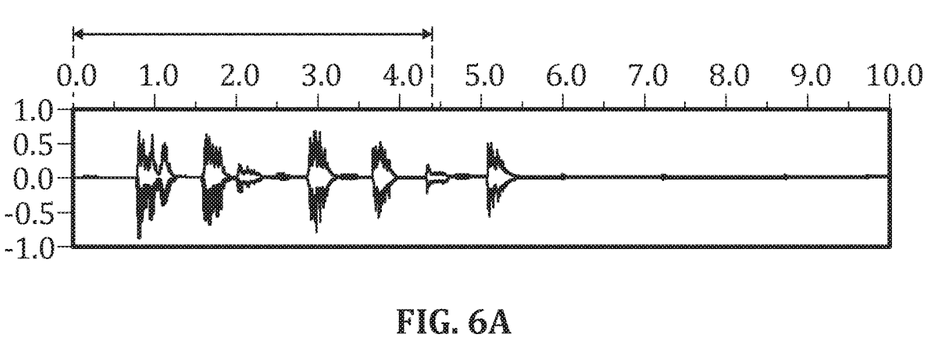
FIGS. 6A-6B illustrate waveforms of a cough detection signal.
Figure 6B:
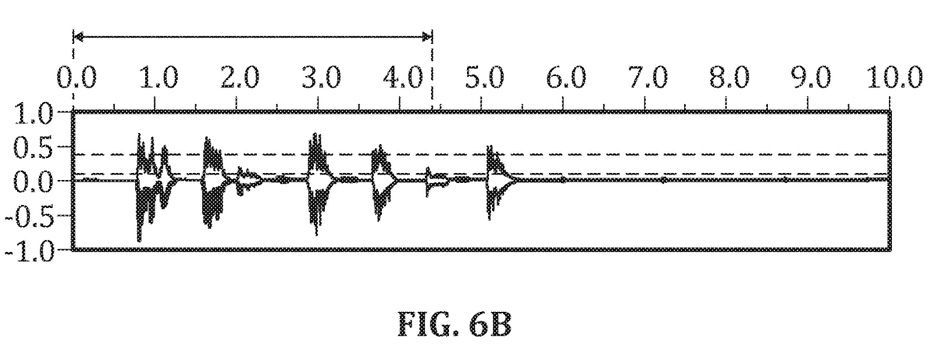
Figure 7A:
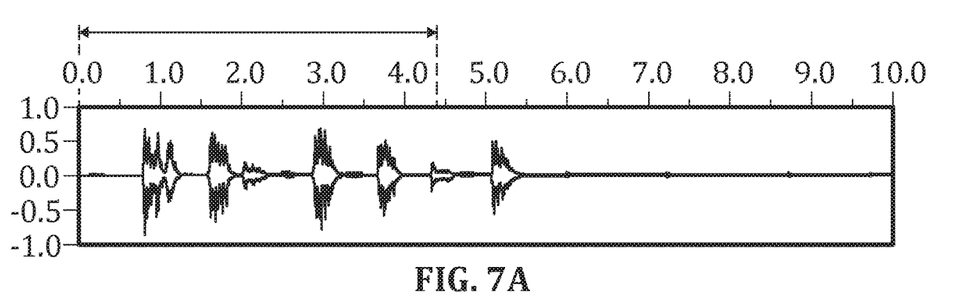
FIGS. 7A-7D illustrate waveforms of a processed cough detection signal using a first signal processing method.

The creation and manufacture of a low cost wearable device to detect human coughing provides challenges in as much as the human cough is not closely modeled by a sonic impulse but rather a time extended 'chirp' of complex frequencies that can last for approximately 200 ms to 400 ms. FIGS. 6-8 illustrate charts corresponding cough detection algorithms that may be used with embodiments of the present disclosure. Embodiments of the present disclosure may employ, for example, two microphones embedded within detection device 405.

The signal illustrated in FIG. 6A represents a subject who made a distinct effort to cough five times over a period of approximately five seconds. Even though the subject attempted to make the five coughs as distinct as possible, a natural 'bounce' occurred in the subject's chest cavity that caused secondary trailing sounds.

The signal in FIG. 6A comprises five major 'chirps' (or regions) corresponding to five detected coughs. The first region comprises a set of two or three distinct sounds, while the second and forth coughs are followed by noise representing the subject's chest bounce. Each person may have his/her own specific sequence of cough/transient waveforms that may vary with, for example, a type, severity and location of lung distress.

FIG. 6B illustrates a first filter that may be applied to the sound to better distinguish coughs from noise (e.g. the subsequent chest bouncing after the cough). The horizontal lines added represent 'threshold' references (e.g. amplitude threshold slicing points) that correspond to a y-axis band-pass type filter for the amplitude of the waveform.

As can be understood form FIG. 6B, the threshold slicing points would render different cough counts depending upon their position on the waveform. For example, an overly low threshold may allow ambient noise to pass through the filter and render the cough counting less effective. On the other hand, an overly high threshold may miss coughs and, consequently, give false counts.

A cough detection device consistent with embodiments of the present disclosure may employ this filter type in cough detection. Threshold slicing may be calibrated, employ additional algorithms, and vary from embodiment to embodiment of the present disclosure. Nevertheless, no matter what threshold values may be set for this filter, there may be an error as large as 50% for time domain detection methods (TDDM). Accordingly, embodiments of the present disclosure that employ this filter type may trigger (i.e. provide a warning notification) on a 'loose' cough count target over an extended period of time.

Various embodiments of the present disclosure may also employ frequency based methods of cough detection and counting. FIG. 7A illustrates the signal of a subject's five cough cycle. The signal may be captured by an AC coupled (DC removed) microphone and amplified by methods available to one of ordinary skill in the art.

Figure 7B:
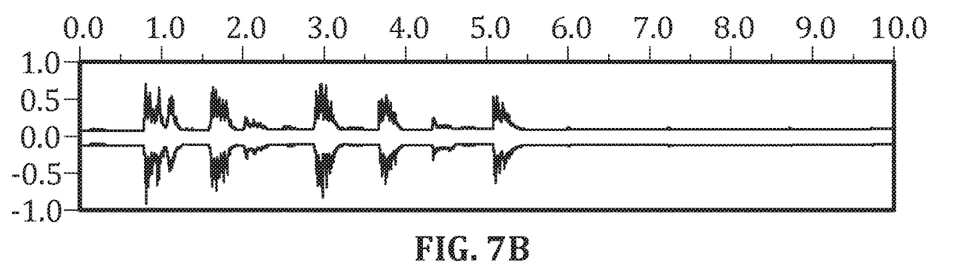
Figure 7C:
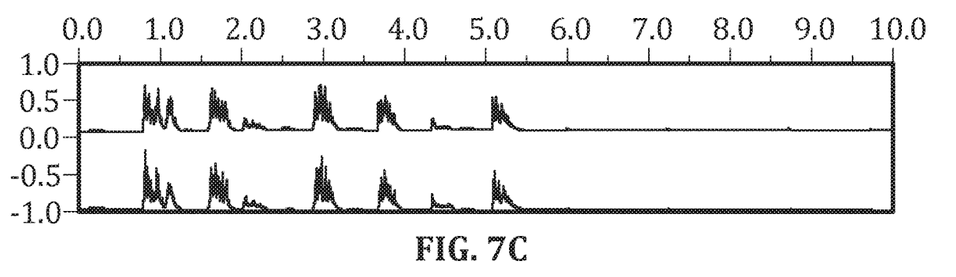
Figure 8A:
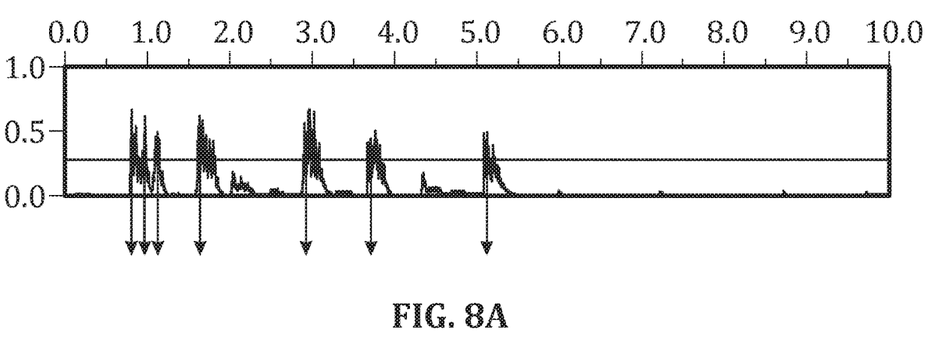
FIGS. 8A-8B illustrate waveforms of a processed cough detection signal using a second signal processing method.
Figure 8B:
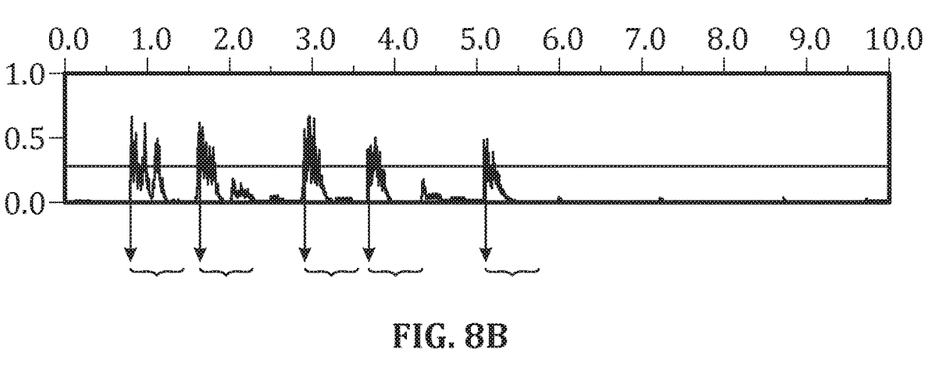

Using a 0V threshold, the signal may be split into positive and negative going voltages as illustrated in FIG. 7B. The upper and lower signal portions may be vary slightly, so both portions should be used in the detection. As illustrated in FIG. 7C, the upper voltage may be preserved as $V_{after}+= V_{before}+$, while the lower waveform may be inverted as $V_{after}-=-(V_{before}-)$.

This signal portions of FIG. 7C may then be passed to an Operational Amplifier to subtract the two portions, yielding $V_{result}=V_{after}+-V_{after}-$. $V_{result}$, depicted in FIG. 7D, may represent the absolute value of the signal illustrated in FIG. 7A.

Figure 7D:
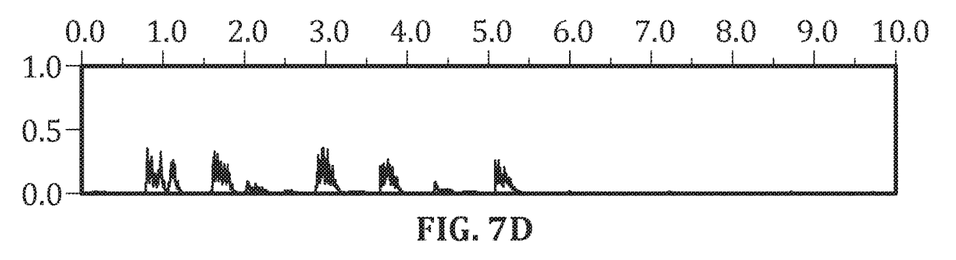

The Signal-to-Noise Ratio (SNR) of the final waveform in FIG. 7D may be improved for better cough detection. For example, applying a straight threshold with a rising edge trigger for counting coughs like the one shown in FIG. 8A, seven coughs may be detected. This may result in an error of 40% since the subject only coughed five times. Knowing that distinct coughs may not occur in intervals of less than, for example, 300 ms, the detection error may be improved.

Consistent with various embodiments of the present disclosure, a disable circuit may be activated upon each rising edge trigger. The disable circuit would effectively prevent or hold the rising edge trigger from activating for at least a predetermined interval of, for example, 300 ms. In this way, the cough count may be incremented by rising edge triggers is not activated for the noise occurring in between the actual coughs. FIG. 8B shows the rising edge trigger counting methods coupled with a disabling circuit at approximately 300 ms intervals. As a result, the rising edge trigger method may now count five coughs.

Embodiments of the present disclosure may further improve cough detection by personalizing the detection device to the individual cough print or waveform of the user. For example, in addition to having stored a small library of recorded coughs associated with different gender, ages, and types of coughs, a cloud-based server may be configured to receive, from the detection device, a cough of the user.

Consistent with embodiments of the present disclosure, when the detection device is initialized, a user may record a cough to the device. The device may then be configured to communicate this recorded cough to an external device, such as a smartphone app or a cloud-based server (e.g., server 410).

The external device, such as the cloud-based server, may then process the received recording and derive a baseline dataset to be used as a comparison point by the detection device. The baseline dataset may comprise, for example, a baseline waveform and/or other data to which a signal may be compared and analyzed for cough detection. In turn, the external device may communicate the baseline waveform back to the detection device. The detection device may, in turn, update its processing algorithms for cough detection based on the updated baseline dataset. In this way, if the user were to lose his detection device or otherwise replace his detection device, the algorithm update may be applied to easily personalize the detection device to the user.

Moreover, as the cough-detection algorithm improves, the software may be continuously upgraded by connection to the external device. The cough-detection algorithm may improve with use of the detection device, as it may learn and build a user-specific cough profile. In accordance to the embodiments of the present disclosure, the connection may not be limited to a wireless connection. For instance, the connection may be a wired, Universal Serial Bus (USB) connection.

V. Detection Device Architecture

By way of no limiting example, FIGS. 9A and 9B illustrate an architecture for two embodiments of the detection device. The first embodiment may be operated by a Field-Programmable Gate Array (FPGA) chip while the second embodiment may be operated with a uProc approach. It should be understood that other architectures are possible (e.g., system on chip (SOC)). The hardware components may be operative to perform the detection, analysis, and processing disclosed in the various embodiments of the present disclosure (e.g., method 500).

Consistent with embodiments of the present disclosure, an AC small amplitude response may be received by a microphone integrated in the detection device. In some embodiments, two microphones may be used (e.g., one on each side of the detection device). Using a weak microphone pendent resting on a user's chest cavity, rather than the sensitive microphone, may facilitate the filtering of non-cough related sounds as distant sounds may not be detected by a weak microphone.

The signal from the microphone may then be passed to a differential amplifier for a single ended output to an analog/digital (A/D) converter. The A/D converter may output a 16 bit word as clocked by clock generation circuitry coupled to the converter.

The clock generation circuitry may produce a clock sample rate (Fs) of 44.1 KHz, corresponding to the Nyquist frequency of the human voice. Accordingly, this Fs may eliminate aliasing of the human voice. Lower sampling rates may be used for cough detection. The clock generation circuitry may also clock the FPGA, uProc, or any other programmable microprocessor with onboard memory (hereinafter "processing unit") that may be designed with the detection device.

The processing unit may have programmed, in its associated memory storage, computer readable code operative to perform method 500 of FIG. 5. For instance, the N-Triggers associated with the processing unit may produce HIGH true signals whenever a given threshold of coughs over a period time is exceeded. The N-Triggers may form a parallel input "OR" which produces an enabling signal that may be passed to the transmitter and modulator.

The enabling signal may enable the transmitter and modulator to power up. The serial stream received from the processing unit may be modulated by the modulator and then broadcast over the transmitter. The serial stream may convey source, destination, and detection information to the modulator and, in turn, the transmitter.

After transmission, the detection device may power down the transmitter and the modulator and reinitialize itself in accordance to method 100 of FIG. 1. Generally, consistent with embodiments of the disclosure, the detection device may comprise program modules that may include routines, programs, components, data structures, and other types of structures that may perform particular tasks or that may implement particular abstract data types. Moreover, embodiments of the disclosure may be practiced with other computer system configurations, including hand-held devices, multiprocessor systems, microprocessor-based or programmable consumer electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

Embodiments of the disclosure, for example, may be implemented as a computer process (method), a computing system, or as an article of manufacture, such as a computer program product or computer readable media.

The computer program product may be a computer storage media readable by a computer system and encoding a computer program of instructions for executing a computer process (e.g., method 500). The computer program product may also be a propagated signal on a carrier readable by a computing system and encoding a computer program of instructions for executing a computer process. Accordingly, the present disclosure may be embodied in hardware and/or in software (including firmware, resident software, microcode, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a random access memory (RAM), a read-only memory (ROM), an erasable programmable read-only memory (EPROM or Flash memory), an optical fiber, and the like. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

VI. Server Architecture

The platform of the present disclosure may be embodied as, for example, but not be limited to, a website, a web application, a desktop application, and a mobile application compatible with a computing device. The computing device may comprise, but not be limited to, a desktop computer, laptop, a tablet, mobile telecommunications device, or a detected local gateway to telecommunications network. Moreover, the platform may be hosted on a centralized server, such as, for example, a cloud computing service.

FIG. 10 is a block diagram of a system including computing device 1000. Consistent with embodiments of the disclosure, the aforementioned memory storage and processing unit may be implemented in a computing device, such as computing device 1000 of FIG. 10. Any suitable combination of hardware, software, or firmware may be used to implement the memory storage and processing unit. For example, the memory storage and processing unit may be implemented with computing device 1000 or any of other computing devices 1018, in combination with computing device 1000. The aforementioned system, device, and processors are examples and other systems, devices, and processors may comprise the aforementioned memory storage and processing unit, consistent with embodiments of the disclosure.

With reference to FIG. 10, a system consistent with embodiments of the disclosure may include a computing device, such as computing device 1000. In a basic configuration, computing device 1000 may include at least one processing unit 1002 and a system memory 1004. Depending on the configuration and type of computing device, system memory 1004 may comprise, but is not limited to, volatile (e.g. random access memory (RAM)), non-volatile (e.g. read-only memory (ROM)), flash memory, or any combination. System memory 1004 may include operating system 1005, one or more programming modules 1006, and may include a program data 1007. Operating system 1005, for example, may be suitable for controlling computing device 1000's operation. In one embodiment, programming modules 1006 may include for example, user interface application 1020. User interface application 1020 may be operative to provide and/or communicate the data necessary to cause a display and corresponding functionality of a user interface on a mobile application or web application associated with the platform. Furthermore, embodiments of the disclosure may be practiced in conjunction with a graphics library, other operating systems, or any other application program and is not limited to any particular application or system. This basic configuration is illustrated in FIG. 10 by those components within a dashed line 1008.

Computing device 1000 may have additional features or functionality. For example, computing device 1000 may also include additional data storage devices (removable and/or non-removable) such as, for example, magnetic disks, optical disks, USB storage, or tape. Such additional storage is illustrated in FIG. 10 by a removable storage 1009 and a non-removable storage 1010. Computer storage media may include volatile and nonvolatile, removable and non-removable media implemented in any method or technology for storage of information, such as computer readable instructions, data structures, program modules, or other data. System memory 1004, removable storage 1009, and non-removable storage 1010 are all computer storage media examples (i.e., memory storage.)

Computing device 1000 may also have input device(s) 1012 such as a keyboard, a mouse, a pen, a sound input device, a touch input device, etc. Output device(s) 1014 such as a display, speakers, a printer, etc. may also be included. The aforementioned devices are examples and others may be used.

Computing device 1000 may also contain a communication connection 1016 that may allow device 1000 to communicate with other computing devices 1018, such as over a network in a distributed computing environment, for example, an intranet or the Internet. Communication connection 1016 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 1004, including operating system 1005. While executing on processing unit 1002, programming modules 1006 (e.g. user interface application 1020) may perform processes associated with the enablement of the mobile and web applications of the platform. The aforementioned process is an example, and processing unit 1002 may perform other processes. Other programming modules that may be used in accordance with embodiments of the present invention may include electronic mail and contacts applications, word processing applications, spreadsheet applications, database applications, slide presentation applications, drawing or computer-aided application programs, etc.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, multiprocessor systems, microprocessor-based or programmable consumer electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer storage, a random access memory (RAM), a read-only memory (ROM), an erasable programmable read-only memory (EPROM or Flash memory), an optical fiber, and the like. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, USB storage devices, or a CD-ROM, a carrier wave from the Internet, or other forms of RAM or ROM. Further, the disclosed methods' stages may be modified in any manner, including by reordering stages and/or inserting or deleting stages, without departing from the disclosure.

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as example for embodiments of the disclosure.

I claim:

1. A system comprising:
a wearable cough detection device comprising:
    at least one microphone,
    a first communications module, wherein the first communications module is configured for bi-directional communication with an intermediary device;
    a first memory storage,
    a first processing unit associated with the at least one microphone, the first communications module, and the first memory storage, wherein the first processing unit is operative to:
        transition from a passive detection state to an active detection state,
        receive a signal from the at least one microphone,
        perform a first set of processing operations, wherein the first set of processing operations enable the cough detection device to:
            determine whether the received signal comprises a cough, and
            determine, upon detection of the cough within the received signal, whether cough data associated with the received signal meets a threshold requirement for transmitting the cough data to the intermediary device, and
        transmit, via the first communications module, to the intermediary device, the cough data associated with the received signal upon a determination that the cough data has met the threshold requirement for transmission, wherein a transmission of the cough data comprises a transmission of a waveform associated with the detected cough, and
    a housing for the at least one microphone, the memory storage, the communications module, and the processing unit, wherein the housing is designed to be worn by a user; and
the intermediary device comprising:
    a second communications module, wherein the communications module is configured for bi-directional communication with the cough detection device and a remote server,
    a second memory storage, and
    a second processing unit associated with the communications module and the memory storage, wherein the second processing unit is operative to:
        receive baseline data associated with at least one baseline waveform from the remote server,
        receive, via the communications module, the cough data,
        perform a second set of processing operations, wherein the second set of processing operations enable the intermediary device to:
            compare the received cough data to the at least one baseline waveform, and
            determine whether to trigger a communication, and
        enable an alert to be triggered in accordance to at least one alert setting.

2. The system of claim 1, wherein the detection of the cough in the received signal by the cough detection device during a performance of the first set of processing operations comprises a detection of a cough consistent with a user profile of the user.

3. The system of claim 1, wherein a comparison, by the intermediary device, of the cough data to the at least one waveform comprises the comparison of the waveform associated with the detected cough to the at least one baseline waveform.

4. The apparatus of claim 1, wherein the first processing unit is further operative to:
    initialize, within the active detection state, a timer set for a predetermined period of time, and
    initialize a counter.

5. The apparatus of claim 4, wherein the first processing unit is further operative to increment the counter in response to the determination the signal received from the at least one microphone comprises the cough.

6. The apparatus of claim 5, wherein the first processing unit being operative to transmit the cough data comprises the processing unit being operative to transmit the cough data upon a threshold count being exceeded by the counter and a threshold time being exceeded by the timer.

7. The system of claim 1, wherein the at least one alert setting corresponds to a determination that the comparison of the cough data to the at least one baseline waveform indicates an exacerbation event.

8. The system of claim 1, further comprising:
the remote server being configured to:
    receive the cough data from the intermediary device,
    perform a third set of processing operations associated with the cough data.

* * * * *